United States Patent [19]
Takahashi et al.

[11] Patent Number: 5,650,406
[45] Date of Patent: Jul. 22, 1997

[54] ADAMANTANE DERIVATIVE, PROCESS FOR PRODUCING THE SAME, AND USE THEREOF

[75] Inventors: Nobuyuki Takahashi; Daisuke Mochizuki, both of Shizuoka, Japan

[73] Assignee: Asahi Kasei Kogyo Kabushiki Kaisha, Osaka, Japan

[21] Appl. No.: 702,453

[22] PCT Filed: Apr. 17, 1995

[86] PCT No.: PCT/JP95/00740

§ 371 Date: Oct. 8, 1996

§ 102(e) Date: Oct. 8, 1996

[87] PCT Pub. No.: WO95/28390

PCT Pub. Date: Oct. 26, 1995

[30] Foreign Application Priority Data

Apr. 18, 1994 [JP] Japan ................................. 6-078687

[51] Int. Cl.$^6$ ................. A61K 31/55; C07D 223/14; C07D 295/096
[52] U.S. Cl. ................. 514/183; 514/216; 514/295; 540/593; 546/97
[58] Field of Search ................. 514/183, 216, 514/295; 540/593; 546/97

[56] References Cited

U.S. PATENT DOCUMENTS

| | | |
|---|---|---|
| 3,328,390 | 6/1967 | Grogan . |
| 3,560,481 | 2/1971 | Berezin . |
| 4,379,160 | 4/1983 | Harfenist et al. . |
| 4,557,865 | 12/1985 | Georgiev et al. . |

FOREIGN PATENT DOCUMENTS

| | | |
|---|---|---|
| 0 661 271 | 7/1995 | European Pat. Off. . |
| 2 155 925 | 10/1985 | United Kingdom . |
| 9406773 | 3/1994 | WIPO .................. C07D 221/24 |

OTHER PUBLICATIONS

V. Georgiev et al., "New Substituted 4–Azatricyclo [4.3.1.1$^{3,8}$] undecane Derivatives", Jul.–Aug. 1986, vol. 23, pp. 1023–1025.

C. Grogan, "w–Azabicyclic Butyrophenones", Jul. 1967, vol. 10, pp. 621–623.

E. Novoselov et al., "Synthesis and reactions of oxaziridines. Adamantane–2–spiro–3'–oxaziridine and its N–alkyl derivatives", Zh. Org. Khim, 1985, vol. 21, No. 1, pp. 107–113.

Chemical Abstracts vol. 122, 1995, abstract No. 213953n.

*Primary Examiner*—Jacqueline Haley
*Attorney, Agent, or Firm*—Young & Thompson

[57] ABSTRACT

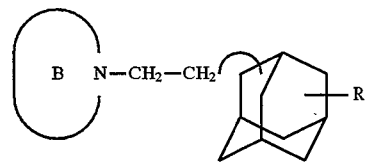

(1)

A compound represented by general formula (1) or an innocuous salt thereof, a process for producing the same, and a schizophrenia remedy containing the same as the active ingredient (wherein the nitrogeneous ring B represents 3-azabicyclo [3.2.2] nonan-3-yl or 4-azatricyclo [4.3.1.1$^{3,8}$] undecan-4-yl; and R represents hydrogen, lower alkyl, lower alkoxy, hydroxy or halogen). The above compound and salt have a high affinity for sigma-binding sites and are useful as an antischizophrenic drug.

18 Claims, No Drawings

ADAMANTANE DERIVATIVE, PROCESS FOR PRODUCING THE SAME, AND USE THEREOF

This is a national stage application of PCT/JP5/00740 filed Apr. 17, 1995 and published as WO95/28390.

FIELD OF THE INVENTION

The present invention relates to an adamantane derivative having antischizophrenic action, process for producing the same, and pharmaceutical use thereof.

PRIOR ARTS

A σ-receptor has been defined as one of the opioid receptor including with μ-, δ- and κ-receptor. At present, the σ-receptor is classified not as opiate but as an independent receptor because an opioid antagonist haloxon has no affinity to σ-receptor.

Psychotomimetic drug phencyclidine has affinities for σ-receptor other than N-methyl-D-aspartic acid (NMDA) receptor, and antipsychotic drug haloperidol has been known to bind strongly with σ-receptor other than dopamine receptor. Therefore, σ-receptor may participate psychic function.

Recently, antischizophrenic drugs with less side effects such as limcazol (Japan. Pat. Unexam. Publ. No. 55-64585) and BMY-14802 (British Patent 2155925) have been developed, and these have been confirmed to show affinity to σ-receptor.

U.S. Pat. No. 4,557,865 discloses a compound of the formula

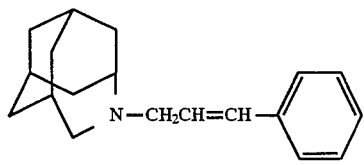

U.S. Pat. No. 3,328,390 also discloses a compound of the formula

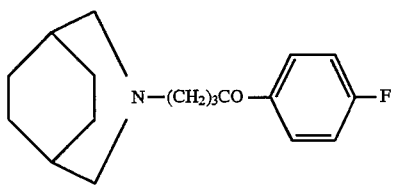

In the above prior arts, neither descriptions on affinities for σ-receptor nor suppression of apomorphine induced climbing model were disclosed.

PROBLEMS TO BE SOLVED BY THE INVENTION

Development of new type of antischizophrenic drugs having different mechanism of action of the known dopamine antagonists has been required.

Means for solving the problems

In the course of screening pharmacological activities of novel synthesized compound, we have found that adamantane derivative of the following general formula (1) has high affinity on σ-receptor without indicating affinities on neurotransmission receptors such as dopamine ($D_1$ and $D_2$) receptors and serotonin (5-$HT_1$ and 5-$HT_2$) receptors, and shows effectiveness for suppressire action of apomorphine induced climbing which was applied for evaluation of antischizophrenic durg. The present invention has been completed upon the above findings.

An object of the present invention is to provide a compound of the formula

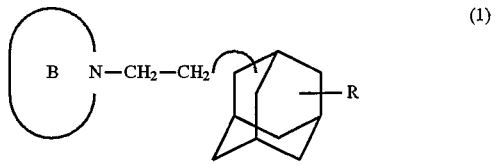

wherein heterocycling group B is 8-azabicyclo[3.2.2]nonane-3-yl or 4-azatricyclo[4.3.1.1$^{3,8}$]undecane-4-yl, and R is hydrogen, lower alkyl, lower alkoxy, hydroxy or halogen. [hereinafter sometimes designates as the compound (1)] or nontoxic salt thereof.

Another object of the present invention is to provide a process for producing the compound of the above formula (1) or nontoxic salt thereof comprising reducing a carbony of the formula

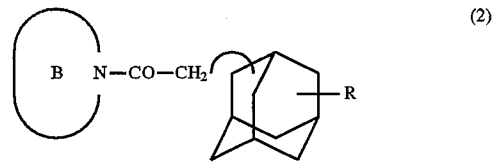

wherein heterocyclic group B and R have the same meanings hereinbefore.

Further object of the present invention is to provide a medicament for treatment of schizophrenia containing the compound of the formula (1) hereinbefore or nontoxic salt thereof as an active ingredient.

Examples of a group R defined in the formula (1) hereinbefore are hydrogen, lower alkyl, lower alkoxy, hydroxy or halogen. The above substituents may be substituted in any position of carbon atom in adamantane ring. Lower alkyl means alkyl of $C_{1-4}$ which may have branched chain, for example, methyl, ethyl, propyl, isopropyl, butyl, isobutyl, sec-butyl and tert-butyl. Lower alkoxy means alkoxy of $C_{1-4}$ which may have branched chain, for example, methoxy, ethoxy, propoxy, is opropoxy, butoxy. isobutoxy, sec-butoxy and tert-butoxy. Halogen means chlorine, bromine, fluorine, etc.

Binding position of adamantyl and a group —$CH_2$ $CH_2$— in the formula (1) can be at any position of carbon in the said ring. In case that R is a substituent group other than hydrogen, a stereoisomer will exist depending upon the position of the substituent. In the present invention, not only a mixture of stereoisomer but also a stereoisomer separated by known method is included.

Examples of the compound (1) of the present invention are as follows.

2 -(2-adamantyl) ethyl derivative of the formula (11)

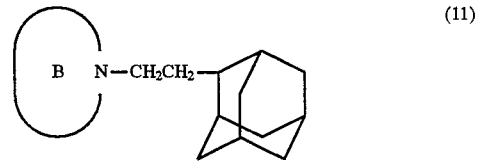

wherein heterocyclic group B has the same meaning hereinbefore, or nontoxic salt thereof.

2-(1-adamantyl) ethyl derivative of the formula (12)

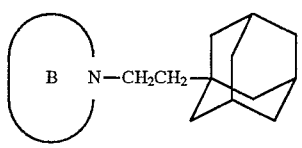

wherein heterocyclic group B has the same meaning hereinbefore, or nontoxic salt thereof.

2-(5-substituted-2-adamantyl) ethyl derivative, a stereoisomer or mixture thereof, of the formula (13)

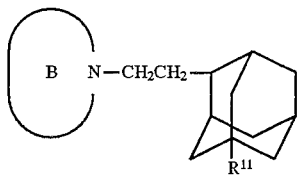

wherein $R^{11}$ is lower alkyl, lower alkoxy, hydroxy or halogen, and heterocyclic group B has the same meaning hereinbefore, or nontoxic salt thereof.

2-(3-substituted-1-adamantyl) ethyl derivative of the formula (14)

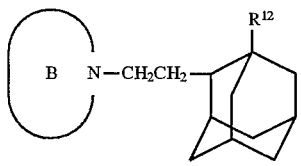

wherein $R^{12}$ is lower alkyl, lower alkoxy, hydroxy or halogen, and heterocyclic group B has the same meaning hereinbefore, or nontoxic salt thereof.

Examples of 2-(2-adamantyl) ethyl derivative are
3-[2-(2-adamantyl)ethyl]-3-azabicyclo[3.2.2] nonane, and
4-[2-(2-adamantyl)ethyl]-4-azatricyclo[4.3.1.1$^{3,8}$] undecane.

Examples of 2-(1-adamantyl) ethyl derivative are
3-[2-(1-adamantyl)ethyl]-3-azabicyclo[3.2.2] nonane, and
3-[2-(1-adamantyl)ethyl]-4-azatricyclo[4.3.1.1$^{3,8}$] undecane.

Examples of stereoisomer of 2-(5-substituted-2-adamantyl)ethyl derivative or mixture thereof are
3-[2-(5-hydroxy-2-adamantyl)ethyl]-3-azabicyclo[3.2.2] nonane.
3-[2-(5-chloro-2-adamantyl)ethyl]-3-azabicyclo[3.2.2] nonane,
3-[2-(5-methoxy-2-adamantyl)ethyl]-3-azabicyclo[3.2.2] nonane,
4-[2-(5-hydroxy-2-adamantyl)ethyl]-4-azatricyclo [4.3.1.1$^{3,8}$] undecane,
4-[2-(5-chloro-2-adamantyl)ethyl]-4-azatricyclo [4.3.1.1$^{3,8}$] undecane, and
4-[2-(5-methoxy-2-adamantyl)ethyl]-4-azatricyclo [4.3.1.1$^{3,8}$] undecane, stereoisomer or mixture thereof.

Examples of 2-(3-substituted-1-adamantyl)ethyl derivative are
3-[2-(3-methyl-1-adamantyl)ethyl]-3-azabicyclo[3.2.2] nonane, and
4-[2-(3-methyl-1-adamantyl)ethyl]-4-azatricyclo [4.3.1.1$^{3,8}$] undecane.

The compound (1) and nontoxic salt thereof of the present invention can be produced by reduction of carbonyl in the compound (2) hereinbefore [hereinafter sometimes designates as compound (2)].

The compouond (2) hereinbefore can be produced by acylating the amine of the formula (3) [hereinafter sometimes designates as amine (8)]

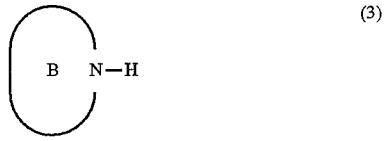

wherein heterocyclic group B has the same meaning hereinbefore, with a carboxylic acid of the formula (4)

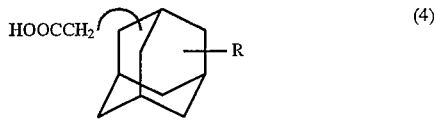

wherein R has the same meanings hereinbefore, or reactive derivative thereof.

The above starting material of amine of the formula (3) is a known compound and is illustrated in the following formula (31) and (32).

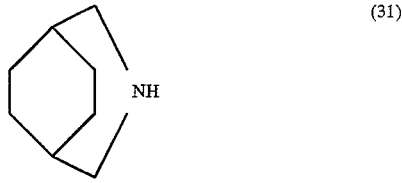

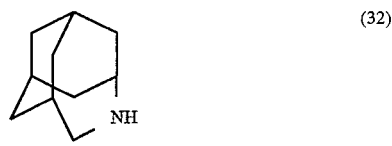

The compound of the formula (31), 3-azabicyclo[3.2.2] nonane is a commercially available compound, and is easily obtainable. 4-azatricyclo [4.3.1.1$^{3,8}$] undecane is a known compound and can be synthesized according to the description in J. Heterocyclic Chem., 23, 1023–1025 (1986).

Preferable examples of the carboxylic acid of the formula (4) are 1-adamantyl acetic acid, 2-adamantyl acetic acid, and 3-methyl-1-adamantyl acetic acid, 5-hydroxy-2-adamantyl acetic acid and 5-methoxy-2-adamantyl acetic acid. These are known compound and can be available commercially or obtainable by synthesis.

A compound including stereoisomer can be used in the form of mixture of stereoisomer or each of the stereoisomer.

The above acylation reaction can be performed by known amidation reaction. Free form of the carboxylic acid (4) can be used in the presence of condensing agent. Examples of the condensing agent are carbodiimides such as N, N'-dicyclohexylcarbodiimide (DCC), 1-ethyl-3-(3'-dimethylaminocyclohexyl) carbodiimide (WSC) and N-cyclohexyl-N'-(4-diethylaminocyclohexyl) carbodiimide, a reagent such as diphenyl-phosphoryl azide, benzotriazoryl-N-hydroxy tris (dimethylamino) phosphonium hexafluoro phosphate and carbonyldiimidazole, and a reagent (Vilsmeier reagent) which is synthesized by a reaction of amide compound such as N-methylformamide or N, N'-dimethylformamide (DMF) with halide such as thionyl chloride, phosphorus oxychloride or phosgene. The other known condensing agent can be used.

Examples of reactive derivative of the carboxylic acid (4) are halide thereof, acid anhydride, acid azide, activated ester and activated amide. Preferable examples are acid halide such as acid chloride and acid bromide, mixed anhydride with acetic acid, pivalic acid, isovaleric acid, trichloroacetic acid and carboxylatemonoalkyl ester, activated ester such as p-nitrophenyl ester, 2, 4-dinitrophenyl ester, trichlorophenyl ester, pentachlorophenyl ester, 1-hydroxy-1H-pyridone ester, N-hydroxysuccinimide ester and N-hydroxyphthalimide ester, and activated amide or pyrazole, imidazole, dimethylpyrazole or benzotriazole.

A reaction using acid halide or acid anhydride of reactive derivative in the above acylating reaction is preferably performed in the presence of deacidification reagent. Examples of deacidification reagent are tertiary organic base such as triethylamine, ethyldiisopropylamine, N,N-dimethylaniline, N-methylmorpholine and pyridine, or known inorganic base such as potassium carbonate and sodium hydroxide.

An amount of ratio in amine (3) and carboxylic acid (4) or reactive derivative thereof is theoretically equimolar, however carboxylic acid (4) or reactive derivative may be used in excess.

Acylating reaction hereinabove is proceeded in an organic solvent which does not act detrimental effect. Examples of organic solvent are chloroform, methylene chloride, tetrahydrofuran (THF), 1,4-dioxane, DMF, N,N-dimethylacetamide and acetone, or mixture thereof. Reaction temperature is not specifically limited, and reaction is usually proceeded at room temperature. Reaction time depends upon reaction temperature and carboxylic acid (4) or reactive derivative thereof and can not be specified, but is atmost up to 48 hours.

Isolation of the compound (2) produced by acylating reaction hereinabove from reaction mixture can be performed by that, in case of reaction solvent being water immiscible organic solvent, after the reaction mixture is washed with aqueous alkaline solution, aqueous acidic solution or saturated sodium chloride solution, organic solvent layer is collected and concentrated, or in case of reaction solvent being water miscible organic solvent, after removal of the solvent, the residue is dissolved in water immiscible organic solvent, then treated the same as of the above to obtain the compound (2). The compound (2) can be purified by known conventional means such as column chromatography and recrystallization.

In the present invention, carbonyl group of the compound (2) is reduced to obtain the compound (1) of the present invention. The reaction can be performed by reducing the compound (2) in inert organic solvent with reducing agent such as lithium aluminium hydride and boron hydride. Examples of inert organic solvent are tetrahydrofuran, diethyl ether (ether), 1, 4-dioxane and pyridine. Reaction temperature is usually under heating preferably with reflux condition. Reaction time depends on reaction temperature and type of reducing agent, and the reaction can be checked by means of thin layer chromatography (TLC), gas chromatography or high performance liquid chromatography (HPLC), accordingly the reaction can be terminated by observing disappearance of the compound (2). The reaction time is, not specified, approximately. 1–10 hours.

The compound (1) produced by the reduction reaction hereinabove can be isolated from the reaction mixture by, in case of reaction solvent being water immiscible organic solvent, after washing the reaction mixture with aqueous acidic solution, aqueous alkaline solution or aqueous saturated sodium chloride solution, concentrating the organic solvent layer, and, in case of reaction solvent being water miscible solvent, after removing the solvent by distillation, and if required dissolving the residue in water immiscible organic solvent, and treating the mixture as same as of the above, to obtain the compound (1).

The compound (1) can also be synthesized by the following method.

A) Production of the compound (1) wherein R is halogen, i.e. a compound (1b) of the formula

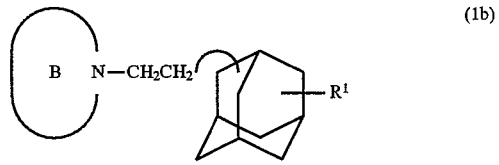

wherein $R^1$ is halogen, and heterocyclic group B has the same meaning hereinberfore:

A compound (1b) can be produced by halogenating the compound (1a) of the formula

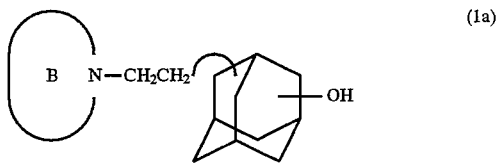

wherein heterocyclic group B has the same meaning hereinberfore.

The above halogenation reaction can be performed by the known halogenating reaction. Examples of the halogenating agent are thionyl chloride, phosphorous trichloride, phosphorus pentachloride, hydrochloric acid, phosphorus oxychloride, hydrobromic acid and diethylamino sulphur trifluoride (DAST). Reaction can be proceeded without solvent or in an inert organic solvent. Another halogenating agent can also be used.

In the above halogenating reaction, reaction temperature is not limited and depends on a type of halogenating agents, preferably at room temperature to reflux temperature. The reaction time depends on reaction temperature and a type of halogenating agents and is, not specified, approximately 48 hours.

Isolation of the compound (1b) from reaction mixture depends on a type of halogenating agents, and can be performed by concentrating the reaction mixture, adding water or pouring the reaction mixture to ice water, adjusting the aqueous layer to alkaline pH, extracting with organic solvent such as dichloromethane and concentrating the organic layer to obtain the compound (1b).

B) Production of the compound (1) wherein R is lower alkoxy, i.e. a compound (1c) of the formula

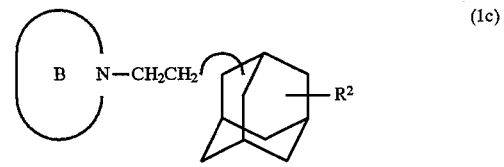

wherein $R^2$ is lower alkoxy, and heterocyclic group B has the same meaning hereinbefore:

The compound (1c) can be prepared by alkylating the compound (1a). The above alkylating reaction can be performed by a known alkylating reaction. Examples of alkylating reaction is a reaction using alkyl halide in an inert organic solvent in the presence of deacidification reagent. Examples of deacidification reagent are known tertiary organic base such as triethylamine, ethyl diisopropylamine, N,N-dimethylaniline, N-methylmorpholine and pyridine, and known inorganic base such as sodium hyroxide, sodium hydride and sodiumamide.

Examples of alkyl halide are methyl iodide, ethyl iodide, n-propyl iodide, n-butyl iodide, isopropyl iodide, isobutyl iodide, bromoethane, 1-bromopropane, 2-bromopropane, 1-bromobutane, 2-bromobutane, 1-chloropropane, 2-chloropropane, 1-chlorobutane and 2-chlorobutane. Examples of inert organic solvent are 1, 2-dimethoxyethane (DME), THF, dimethyl-sulfoxide (DMSO) and DMF or mixture thereof. Ratio of the amount of the compound (1a) and alkyl halide is theoretically in equimolar, and conventionally excess amount of alkyl halide is used.

Reaction temperature in the alkylation reaction hereinabove, is not limited and is proceeded at room temperature. Reaction time depends on reaction temperature and type of alkyl halide, and is, not specified, approximately 48 hours.

Isolation of the compound (1c) from the reaction mixture can be made by, in case of reaction solvent being water immiscible organic solvent, after the washing the reaction mixture with aqueous alkali or saturated sodium chloride solution, and concentrating the organic solvent, or in case of reaction solvent being water miscible organic solvent, removing the organic solvent, dissolving the residue in water immiscible organic solvent, and treating as same as of the above to obtain the compound (1c). Another alkylating reagent such as dimethyl sulfate can also be used.

The compound (1) can be purified further, if required, for example, by conventional known purification method such as column chromatography and recrystallization.

In the present invention, when the compound (1) of the present invention is synthesized as a mixture of stereoisomer, each stereoisomer can be isolated by known methods such as silica gel column chromatography and HPLC. In case that stereoisomer of the starting material carboxylic acid (4) or reactive derivative thereof is used, the compound (1) of the present invention can be synthesized as a stereoisomer.

In the present invention, when a compound of the present invention (1) is disclosed, the compound can easily be synthesized by combining prior known reactions other than the process hereinabove explained.

The thus produced compound (1) of the present invention can be converted, if required, to a pharmaceutically acceptable nontoxic salt thereof.

Examples of those salts are acid addition salt, and are inorganic salt of hydrochloride, sulfate and phosphate, and organic salt of acetate, propionate, tartarate, citrate, glycolate, gluconate, succinate, malate, glutamate, aspartate, metanesulfonate, mandelate, p-toluenesulfonate, maleinaate and fumarate.

The conapound (1) of the present invention or nontoxic salt thereof showed no death in an intraperitoneal administration of 100 mg/kg in rat and the compound can be said quite safety to use as a medicament.

The compound (1) of the present invention or nontoxic salt thereof used in the form of formulation and is administered per oral or parenterally such as injection including drop infusion. An amount of administration may be varied by dosage form, age, body weight and condition of recipients, and is 0.01 mg–100 mg/adult/day.

Effect of the invention

Pharmacological action of the compound (1) of the present invention is explained as follows.

1) Binding activities to σ-receptor:

Binding activities of a compound (1) of the present invention or nontoxic salt thereof of σ-receptor are assayed by the following methods. Results are shown in Table 1.

(A) Binding activities of the compound (1) of the present invention on σ-receptor are assayed by a method described in E. Weber et al., Proc. Natl. Acad. Sci. U.S.A., Vol. 83, 8784–8788 (1986).

Immediately after decapitation of Sprague-Dowley rats, male, 7 weeks age, supplied by Charles River Inc., the brains were collected and whole brains except cerebella were homogenized with 50 mM Tris-HCl buffer solution (pH 8.0, TH buffer solution) and centrifuged at 700 x g for 10 minutes. The supernatant was centrifuged at 48,000 x g for 15 minutes, and precipitates were suspended in TH buffer solution which was incubated at 37° C. for 20 minutes. The suspension was centrifuged at 48,000 x g for 15 minutes and the thus obtained precipitates were suspended in TH buffer solution to prepare a membrane standard preparation.

The standard preparation of membrane (approx. 600 μg protein) and [$^3$H] 1, 3-di(2-tolyl) guanidine (DTG, New England Nuclear Corp.)(final concentration: 3 nM) were reacted at 25° C. for 60 minutes, and the reaction was stopped by suction filtering through Whatman GF/C filter. Radioactivity adsorbed on the filter was measured by Scintillation Counter, and the value obtained was set as total binding amount. Non specific binding amount (NB) was set up by measuring the assay mixture with adding 10 μM haloperidol. Binding assay of the sample was performed by adding the sample in place of adding haloperidol in the assay system to obtain the assay result (DTB).

(B) Ki-value (affinity of the drug to receptor)

Binding inhibitory rate of the sample at constant concentration was calculated by the following equation.

Binding inhibition rate $(\%)=[1-(DTB-NB) \div (TB-NB)] \times 100$

Binding inhibition rates at various concentrations from high to low concentrations were measured in each sample, and plotted a logarithmic value of concentration on a transverse and binding inhibition rate on an ordinate, then drawing a curve by the nonlinear method of least sqares to obtain $IC_{50}$ value.

Ki value is calculated by the following equation.

$$Ki=(IC_{50}) \div [1+(L)/Kd]$$

wherein (L) is a concentration of radioactive ligand (3 nM) in the experiment, Kd is concentration of affinity of radioactive ligand for receptor (10.6 nM) and $IC_{50}$ is a concentration of drug which inhibits at 50% for binding receptor and radioactive ligand.

(C) Binding activity:

Result of binding activity of the compound of the present invention to σ-receptor is shown in Table 1.

TABLE 1

| Binding activity for σ-receptor | |
| --- | --- |
| Compound No. in Examples (hydrochloride) | Sigma [$^3$H] DTG Ki (nM) |
| 1 | 0.34 |
| 2 | 0.50 |
| 3 | 0.27 |
| 4 | 1.03 |
| 5 | 0.19 |
| 6 | 0.45 |

TABLE 1-continued

Binding activity for σ-receptor

| Compound No. in Examples (hydrochloride) | Sigma [$^3$H] DTG Ki (nM) |
| --- | --- |
| 7 | 0.26 |
| 8 | 1.23 |
| 9 | 0.55 |
| 10 | 0.63 |
| 11 | 0.20 |
| 12 | 0.29 |

As shown hereinabove, the compound of the present invention has strong affinity to σ-receptor and has no affinity to neurotransmition receptors such as dopamine ( $D_1$ and $D_2$) receptors and serotonin (5-$HT_{1A}$ and 5-$HT_2$) receptors.

2. Suppressire activity of apomorphine induced climbing

Administering dopamine agohist, apomorphine in mouse resulted various abnormal behaviors, and especially, a climbing the cage has been known to be correlated with human schizophrenia. Therefore, a drug showing suppressire activity for apomorphine induced climbing in mice can be presumed to be effective as antischizophrenia activity on humans.

The compounds of the present invention were administered orally in ICR mice, male (Charles River Corp.), and after 1 hour, apomorphine 2 mg/kg was administered subcutaneously. Climbing behaviors of 3 minutes after 20–23 minutes of apomorphine administration were observed. Climbing behavior was observed by entering the mice in stainless steel made wire netting cage and measuring time remaining above the upper part of half part of the cage at observing. A climbing time of apomorphine single administered group is set as 100% and shortened time by administering the drug is shown in suppression rate.

Result of suppressire action of the compound of the present invention on apomorphine induced climbing is shown in Table 2.

TABLE 2

Suppressive action on apomorphine inducing climbing

| Sample Compound No. in Examples (hydrochloride) | Suppressive rate (mg/kg, p.o.) |
| --- | --- |
| 1 | 62% (30) |
| 7 | 60% (30) |
| 8 | 78% (30) |

As shown hereinabove, the compound (1) of the present invention suppressed apomorphine induced climbing. These results indicated that the compound (1) of the present invention or nontoxic salt thereof has strong antischizophrenia activity.

EXAMPLES

The present invention is explained in detailes by the referential examples and examples hereinbelow, however the present invention is not limited within these examples. Mass spectrum (MS) data and Nuclear Magnetic Resonance spectrum data ($^1$H-NMR) of the compounds obtained by these examples are shown in Tables 3–4.

Referential example 1

Methyl 2-adamantylidene acetate:

Methanol solution (500 ml) of 2-adamantanone 115.00 g (0.77 mol) and methyl diethylphosphono acetate 210.78 ml (1.15 mol) was cooled at 0 ° C. 28% methanol solution of sodium methylate 371.7 g were added dropwise with gradually changing temperature to room temperature and stirred for 4 hours. Reaction mixture was concentrated in vacuo. Water was added thereto and the mixture was extracted with ethyl acetate, then dried by adding anhydrous sodium sulfate. After removal of the drying agent, the filtrate was concentrated in vacuo. Residue was purified by silica gel column chromatography (Wako gel, C200, n-hexane: ethyl acetate=20:1) to obtain the product.

Yield: 157.70 g (Yield: 100%)

Referential example 2

2-adamantyl acetic acid methyl ester:

10% palladiuim carbon 2.90 g and ammonium formate 178 g (2.8 mol) were added to methanol solution 1150 ml of methyl 2-adamantylidene acetate 145 g (0.70 mol), and stirred for 3 hours at room temperature. Palladium carbon was removed from the reaction mixture and the filtrate was concentrated in vacuo. Water was added to the residue, and extracted with ethyl acetate. The extract was dried by adding anhydrous sodium sulfate. After filtering the drying agent, the filtrate was concentrated in vacuo to obtain the product.

Yield: 146.41 g (Yield: 100%)

Referential example 3

2-adamantyl acetic acid:

Aqueous 2.5 N sodium hydroxide solution 433 ml was added to methanol solution 1125 ml of 2-adamantyl acetic acid methyl ester 150 g (0.72 mol) and stirred at room temperature for 6 hours. Reaction mixture was concentrated in vacuo. Aqueous sodium bicarbonate solution was added to the residue and the mixture was washed with ether. Aqueous layer was adjusted to pH 1 by adding 12 N hydrochloric acid, extracted with ethyl acetate and dried with anhydrous sodium sulfate.

Yield: 129.39 g (Yield: 92%)

Example 1

3-[2-(2-adamantyl) ethyl]-3-azabicyclo[3.2.2] nonane:

Dichloro methane 10 ml solution of 3-azabicyclo[3.2.2] nonane 0.25 g and 2-adamantyl acetic acid 0.43 g was cooled to 0° C., added WSC 0.54 g thereto, gradually changed temperature to room temperature, then stirred for 19 hours.

Reaction mixture was washed with saturated sodium chloride solution and dried by adding anhydrous sodium sulfate. After removing the drying agent, the flitrate was concentrated in vacuo to obtain crude 3-(2-adamantylacetyl)-3-azabicyclo[3.2.2] nonane.

The compound was added without purification into THF 30 ml solution of lithium aluminium hydride 0.23 g and refluxed for 1.5 hour. Reaction mixture was cooled, removed the insolubles by adding water and the filtrate was concentrated in vacuo. The thus obtained residue was purified using silica gel column chromatography (Wako gel, C200, chloroform:acetone:methanol=5:1:0.1) to obtain the product.

Yield: 0.19 g (Yield: 33%)

Two molar amount of methanol solution of hydrogen chloride were added to the compound hereinabove, concentrated the solution to crystallize by adding ether to obtain the hydrochloride of the product.

Referential example 4

Methyl 5-hydroxy-2-adamantylidene acetate:

DME 5 ml solution of methyl diethylphosphono acetate 0.200 ml was cooled at −10° C., added sodium hydride ( 60%, oil suspension) 54.3 mg and stirred at −10° C. for 1 hour. DME 5 ml solution of 5-hydroxy-2-adamantanone 150 mg was added thereto and stirred at the same temperature for 1.5 hour. Water was added to the reaction mixture and DME was removed by concentration in vacuo. Residue was extracted with chloroform and dried by adding anhydrous sodium sulfate. After removal of the drying agent, the filtrate was concentrated in vacuo, and the residue was purified by means of silica gel column chromatography (Wako gel, C200, chloroform) to obtain the product.

Yield: 180 mg (Yield: 90%)

Referential example 5

5-hydroxy-2-adamantyl acetic acid methyl ester:

10% palladiium carbon 18.0 mg was added in methanol solution 5 ml of methyl 5-hydroxy-2-adamantylidene acetate 179.9 mg, and subjected to catalytic hydrogenation under stream of hydrogen gas for 2.5 hours under normal temperature and normal pressure. Palladium carbon was removed by the reaction mixture and the liltrate was concentrated in vacuo to obtain colorless oily product as a mixture of steroisomer. (a mixture of stereoisomer 1:1 measured by gas chromatography)

Yield: 166.3 mg (Yield: 92%)

Referential example 6

5-hydroxy-2-adamantyl acetic acid:

Aqueous 2.5 N sodium hydroxide solution 0.49 ml was added to methanol 10 ml solution of 5-hydroxy-2-adamantyl acetic acid methyl ester 181.5 mg and stirred at room temperature for 14 hours. Reaction mixture was concentrated in vacuo. Saturated sodium bicarbonate solution was added to the residue and washed with ether. Aqueous layer was adjused to pH 1 by adding 12 N hydrochloric acid, and extracted with ethyl acetate, then dried by adding anhydrous sodium sulfate. After removal of the drying agent, the filtrate was concentrated in vacuo to obtain the product as a mixture of stereoisomer. (a mixture of stereoisomer 1:1 measured by gas chromatography)

Yield: 150 mg (Yield: 88%)

Example 2

3-[2-(5-hydroxy-2-adamantyl) ethyl]-3-azabicyclo[3.2.2] nonane:

Dichloro methane 5 ml solution of 3-azabicyclo[3.2.2] nonane 65.6 mg and 5-hydroxy-2-adamantyl acetic acid 100 mg obtained in referential example 6 was cooled to 0° C. added WSC 119 mg thereto, and stirred for 24 hours after gradually changed temperature to room temperature.

Reaction mixture was washed with saturated sodium chloride solution and dried by adding anhydrous sodium sulfate. After removing the drying agent by filtration, the filtrated solution was concentrated in vacuo to obtain crude 3-(5-hydroxy-2-adamantyl acetyl)-3-azabicyclo-[3.2.2] nonane, which was, without purification, added in THF 5ml solution of lithium aluminium hydride 21.7 mg, and refluxed for 4 hours. Reaction mixture was cooled, and the insolubles were removed by filtration with adding water, then the filtrate was concentrated in vacuo. The thus obtained residue was purified using silica gel column chromatography (Wako gel, C200, chloroform: methanol=75:1–5:1) to obtain the product as a mixture of stereoisomer. (a mixture of stereoisomer 1:1 measured by gas chromatography)

Yield: 124 mg (Yield: 86%)

Hydrochloride was obtained by the same procedure as of in example 1.

Example 3

3-[2-(5-chloro-2-adamantyl)ethyl]-3-azabicyclo[3.2.2] nonane:

Thionyl chloride 5 ml was added to 3-[2-(5-hydroxy-2-adamantyl) ethyl]-3-azabicyclo[3.2.2] nonane 59.5 mg obtained in example 2 and refluxed for 16 hours. Reaction mixture was concentrated in vacuo and saturated sodium bicarbonate was added to the residue to set to alkaline pH, then extracted with chloroform. The extract was dried by adding ahnydrous sodium sulfate. After removal of drying agent, the filtrate was concentrated in vacuo, and the residue was purified by means of silica gel column chromatography (Wako gel, C200, chloroform: acetone=15:1) to obtain the product as a mixture of stereoisomer. (a mixture of stereoisomer 1:1 measured by gas chromatography)

Yield: 37.5 mg (Yield: 59%)

Hydrochloride was obtained by the same procedure as of in example 1.

Referential example 7

5-methoxy-2-adamantanone:

THF 5 ml solution of 5-hydroxy-2-adamantanone 100 mg and methyl iodide 0.113 ml was cooled at 0° C., and sodium hydride (60%, oil suspension) 48.2 mg was added therein, and the temperature of the reaction mixture was gradually changed to room temperature, then stirred for 25 hours. The reaction mixture was cooled again, and water was added thereto, then THF was removed by concentration in vacuo. The thus obtained residue was extracted with chloroform and dried by adding anhydrous sodium sulfate. After separation of the drying agent, the filtrate was concentrated in vacuo. Residue was purified by means of silica gel column chromatography (Wako gel, C200, n-hexane: ethyl acetate=10:1) to obtain the product.

Yield: 57.7 mg (Yield: 54%)

Referential example 8

Methyl 5-methoxy adamantylidene acetate:

DME 2 ml solution of 5-methoxy-2-adamantanone 57.7 mg and methyl diethylphosphono acetic acid 70.6 µl was cooled at 0° C., and sodium hydride (60%, oil suspension) 25.6 mg was added therein, and the temperature of the reaction mixture was gradually changed to room temperature, then stirred for 3.5 hours. The reaction mixture was cooled again, and water was added therein to decompose sodium hydride, then DME was removed by concentration in vacuo. The thus obtained residue was extracted with chloroform and dried by adding anhydrous sodium sulfate. After separation of the drying agent, the filtrate was concentrated in vacuo. Residue was purified by means of silica gel column chromatography (Wako gel, C200, n-hexane: ethyl acetate=10:1) to obtain the product.

Yield: 53.2 mg (Yield: 70%)

Referential example 9

5-methoxy-2-adamantyl acetic acid methyl ester:

10% palladiium carbon 5.3 mg was added in methanol solution 2 ml of methyl 5-methoxy-2-adamantylidene acetate 53.2 mg, and subjected to catalytic hydrogenation under stream of hydrogen gas for 1.5 hours under normal temperature and normal pressure. Palladium carbon was removed by the reaction mixture and the filtrate was concentrated in vacuo to obtain the product as a mixture of steroisomer. (a mixture of stereoisomer 1:1 measured by gas chromatography)

Yield: 50.0 mg (Yield: 93%)

Referential example 10

5-methoxy-2-adamantyl acetic acid:

Aqueous 2.5 N sodium hydroxide solution 0.13 ml was added to methanol 2 ml solution of 5-methoxy-2-adamantyl acetic acid methyl ester 50.0 mg obtained in referential example 9 and stirred at room temperature for 7 hours. Reaction mixture was concentrated in vacuo. Saturated sodium bicarbonate solution was added to the residue and washed with ether. Aqueous layer was adjused to pH 1 by adding 12 N hydrochloric acid, and extracted with ethyl acetate, then dried by adding anhydrous sodium sulfate. After removal of the drying agent, the filtrate was concentrated in vacuo to obtain the product as a mixture of stereoisomer. (a mixture of stereoisomer 1:1 measured by gas chromatography)

Yield: 86.2 mg (Yield: 77%)

Example 4

3-[2-(5-methoxy-2-adamantyl) ethyl]-3-azabicyclo[3.2.2] nonane:

Dichloro methane 5 ml solution of 3-azabicyclo[3.2.2] nonane 32.7 mg and 5-methoxy-2-adamantyl acetic acid 56.4 mg obtained in referential example 10 was cooled to 0° C., added WSC 59.1 mg thereto, and stirred for 25 hours after gradually changed temperature to room temperature.

Reaction mixture was washed with saturated sodium chloride solution and dried by adding anhydrous sodium sulfate. After removing the drying agent by filtration, the filtrated solution was concentrated in vacuo to obtain crude 3-(5-methoxy-2-adamantyl acetyl)-3-azabicyclo-[3.2.2] nonane, which was, without purification, added in THF 5 ml solution of lithium aluminium hydride 10.8 mg, and refluxed for 3 hours. Reaction mixture was cooled, and the insolubles were removed by filtration with adding water, then the filtrate was concentrated in vacuo. The thus obtained residue was purified using silica gel column chromatography (Wako gel, C200, chloroform: acetone: methanol=10:1:0.1) to obtain the product as a mixture of stereoisomer. (a mixture of stereoisomer 1:1 measured by gas chromatography)

Yield: 56.9 mg (Yield: 76%)

Hydrochloride was obtained by the same procedure as of in example 1.

Example 5

3-[2-(1-adamantyl) ethyl]-3-azabicyclo[3.2.2] nonane:

Dichloro methane 5 ml solution of 3-azabicyclo[3.2.2] nonane 100 nag and 1-adamantyl acetic acid 171 mg was cooled to 0° C., added WSC 215 mg thereto, gradually changed temperature to room temperature, then stirred for 24 hours.

Reaction mixture was washed with saturated sodium chloride solution and dried by adding anhydrous sodium sulfate. After removing the drying agent, the filtrate was concentrated in vacuo to obtain crude 3-(1-adamantylacetyl)-3-azabicyclo[3.2.2] nonane.

The compound was added without purification into THF 5 ml solution of lithium aluminium hydride 36.4 mg and refluxed for 6 hours. Reaction mixture was cooled, removed the insolubles by adding water and the filtrate was concentrated in vacuo. The thus obtained residue was purified using silica gel column chromatography (Wako gel, C200, chloroform: acetone=20:1–5:1) to obtain the product.

Yield: 229 mg (Yield: 100%)

Hydrochloride was obtained by the same procedure as of in example 1.

Example 6

3-[2-(3-methyl-1-adamantyl) ethyl]-3-azabicyclo[3.2.2] nonane:

Dichloro methane 5 ml solution of 3-azabicyclo[3.2.2] nonane 100 mg and 3-methyl-1-adamantyl acetic acid 183 mg was cooled to 0° C., added WSC 215 mg thereto, gradually changed temperature to room temperature, then stirred for 21 hours.

Reaction mixture was washed with saturated sodium chloride solution and dried by adding anhydrous sodium sulfate. After removing the drying agent, the liltrate was concentrated in vacuo to obtain crude 3-(3-methyl-1-adamantylacetyl)-3-azabicyclo[3.2.2] nonane.

The compound was added without purification into THF 5 ml solution of lithium aluminium hydride 36.4 mg and refluxed for 4 hours. Reaction mixture was cooled, removed the insolubles by adding water and the filtrate was concentrated in vacuo. The thus obtained residue was purified using silica gel column chromatography (Wako gel, C200, chloroform: acetone=5:1) to obtain the product.

Yield: 236 mg (Yield: 98%)

Hydrochloride was obtained by the same procedure as of in example 1.

Example 7

4-[2-(2-adamantyl) ethyl]-4-azatricyclo[4.3.1.1$^{3.8}$] undecane:

Triethylanaine 0.34 ml was added in dichloro methane 10 ml solution of 4-azatricyclo[4.3.1.1$^{3.8}$] undecane hydrochloride 0.38 g and stirred at 0° C. for 30 minutes. 2-adamantyl acetic acid 0.43 mg and thereafter WSC 0.54 g were added thereto, then the reaction tenaperature was gradually changed to room temperature, and stirred for 22 hours.

Reaction naixture was washed with saturated sodium chloride solution and dried by adding anhydrous sodium sulfate. After removing the drying agent, the filtrate was concentrated in vacuo to obtain crude 4-(2-admantylacetyl)-4-azatricyclo[4.3.1.1$^{3.8}$] undecane.

The compound was added without purification into THF 30 ml solution of lithium aluminium hydride 0.23 g and refluxed for 1.5 hour. Reaction mixture was cooled, removed the insolubles by adding water and the filtrate was concentrated in vacuo. The thus obtained residue was purified using silica gel colunan chronaatography (Wako gel, C200, chloroform: acetone: methanol=10:1:0.1) to obtain the product.

Yield: 0.23 g (Yield: 37%)

Hydrochloride was obtained by the same procedure as of in example 1.

Example 8

4-[2-(5-hydroxy-2-adanaantyl)ethyl]-4-azatricyclo [4.3.1.1$^{3.8}$] undecane:

Triethylamine 81.8 μl was added to dichloro methane 5 ml solution of 4-azatricyclo[4.3.1.1$^{3.8}$] undecane hydrochloride 100 mg and stirred at 0° C. for 30 minutes. WSC 133 mg and thereafter 5-hydroxy-2-adamantyl acetic acid 124 mg obtained in referential example 6 were added thereto, then the reaction temperature was gradually changed to room temperature, and stirred for 43 hours.

Reaction mixture was washed with saturated sodium chloride solution and dried by adding anhydrous sodium sulfate. After removing the drying agent, the filtrate was concentrated in vacuo to obtain crude 4-(5-hydroxy-2-adamantylacetyl)-4-azatricyclo[4.3.1.1$^{3.8}$] undecane.

The compound was added without purification into THF 5 ml solution of lithium aluminium hydride 24.3 mg and refluxed for 5 hours. Reaction mixture was cooled, removed the insolubles by adding water and the filtrate was concentrated in vacuo. The thus obtained residue was purified using silica gel column chromatography (Wako gel, C200, chloroform: methanol=100:1) to obtain the product as a mixture of stereoisomer. (a mixture of stereoisomer 1:1 measured by gas chromatography)

Yield: 88.6 mg (Yield: 50%)

Hydrochloride was obtained by the same procedure as of in example 1.

Example 9

4-[2-(5-chloro-2-adamantyl) ethyl]-4-azatricyclo [4.3.1.1$^{3.8}$] undecane:

Thionyl chloride 5 ml was added to 4-[2-(5-hydroxy-2-adamantyl)-ethyl]-4-azatricyclo[4.3.1.1 $^{3.8}$] undecane 105 mg obtained in example 8 and refluxed for 4 hours. Reaction mixture was concentrated in vacuo and saturated sodium bicarbonate was added to the residue to set to alkaline pH, then extracted with chloroform. The extract was dried by adding ahnydrous sodium sulfate. After removal of drying agent, the filtrate was concentrated in vacuo, and the residue was purified by means of silica gel column chromatography (Wako gel, C200, chloroform: methanol=50:1–20:1) to obtain the product as a mixture of stereoisomer. (a mixture of stereoisomer 1:1 measured by gas chromatography)

Yield: 51.1 mg (Yield: 46%)

Hydrochloride was obtained by the same procedure as of in example 1.

Example 10

4-[2-(5-methoxy-2-adamantyl) ethyl]-4-azatricyclo [4.3.1.1$^{3.8}$] undecane:

Triethylamine 86.9 μl was added to dichloro methane 5 ml solution of 4-azatricyclo[4.3.1.1$^{3.8}$] undecane hydrochloride 88.9 mg and stirred at 0° C. for 30 minutes. WSC 127 mg and thereafter 5-hydroxy-2-adamantyl acetic acid 118 mg obtained in referential example 10 were added thereto, then the reaction temperature was gradually changed to room temperature, and stirred for 21 hours.

Reaction mixture was washed with saturated sodium chloride solution and dried by adding anhydrous sodium sulfate. After removing the drying agent, the filtrate was concentrated in vacuo to obtain crude 4-(5-methoxy-2-adamantylacetyl)-4-azatricyclo[4.3.1.1$^{3.8}$] undecane.

The compound was added without purification into THF 5 ml solution of lithium aluminium hydride 21.6 mg and refluxed for 3 hours. Reaction mixture was cooled, removed the insolubles by adding water and the filtrate was concentrated in vacuo. The thus obtained residue was purified using silica gel column chromatography (Wako gel, C200, chloroform: acetone: methanol=10:1:0.1–5:1:1) to obtain the product as a mixture of stereoisomer. (a mixture of stereoisomer 1:1 measured by gas chromatography)

Yield: 120 mg (Yield: 75%)

Hydrochloride was obtained by the same procedure as of in example 1.

Example 11

4-[2-(1-adamantyl) ethyl]-4-azatricyclo[4.3.1.1$^{3.8}$] undecane:

Triethylamine 65.6 μl was added to dichloro methane 5 ml solution of 4-azatricyclo[4.3.1.1$^{3.8}$] undecane hydrochloride 73.5 mg and stirred at 0° C. for 30 minutes. WSC 106 mg and thereafter 1-adamantyl acetic acid 83.7 mg were added thereto, then the reaction temperature was gradually changed to room temperature, and stirred for 25 hours.

Reaction mixture was washed with saturated sodium chloride solution and dried by adding anhydrous sodium sulfate. After removing the drying agent, the fillrate was concentrated in vacuo to obtain crude 4-(1-adamantylacetyl)-4-azatricyclo[4.3.1.1$^{3.8}$] undecane.

The compound was added without purification into THF 5 ml solution of lithium aluminium hydride 17.9 mg and refluxed for 5 hours. Reaction mixture was cooled, removed the insolubles by adding water and the filtrate was concentrated in vacuo. The thus obtained residue was purified using silica gel column chromatography (Wako gel, C200, chloroform: acetone=5:1) to obtain the product.

Yield: 58.0 mg (Yield: 47%)

Hydrochloride was obtained by the same procedure as of in example 1.

Example 12

4-[2-(8-methyl-1-adamantyl) ethyl]-4-azatricyclo [4.3.1.1$^{3.8}$] undecane:

Triethylamine 63.6 μl was added to dichloro methane 5 ml solution of 4-azatricyclo[4.3.1.1$^{3.8}$] undecane hydrochloride 71.2 mg and stirred at 0° C. for 30 minutes. WSC 102 mg and thereafter 1-adamantyl acetic acid 87.1 mg were added thereto, then the reaction temperature was gradually changed to room temperature, and stirred for 20 hours.

Reaction mixture was washed with saturated sodium chloride solution and dried by adding anhydrous sodium sulfate. After removing the drying agent, the filtrate was concentrated in vacuo to obtain crude 4-(3-methyl-1-adamantylacetyl)-4-azatricyclo[4.3.1.1$^{3.8}$] undecane.

The compound was added without purification into THF 5 ml solution of lithium aluminium hydride 17.8 mg and refluxed for 5 hours. Reaction mixture was cooled, removed the insolubles by adding water and the filtrate was concentrated in vacuo. The thus obtained residue was purified using silica gel column chromatography (Wako gel, C200, chloroform:acetone=5:1) to obtain the product.

Yield: 106 mg (Yield:86%)

Hydrochloride was obtained by the same procedure as of in example 1.

TABLE 3

| Ref. Ex. No | $^1$H-NMR(CDCl$_3$)δ(ppm) | MS |
|---|---|---|
| 1 | 1.8–2.0(12H, m), 2.44(1H, bs), 3.68 (3H, s), 4.06(1H, bs), 5.59(1H, s) | (FAB) 206 (MH+) |
| 2 | 1.5–1.9(13H, m), 2.23(1H, dd, J=7.3, 7.9Hz), 2.46(2H, d, J=7.6Hz), 3.66(3H, s) | (FAB) 208 (MH+) |
| 3 | 1.56(2H, d, J=11.9Hz), 1.6–1.9(12H, m), 2.24(1H, t, J=7.3Hz), 2.50(2H, d, J=7.3Hz) | (FAB) 193 (M–H)– |
| 4 | 1.54(1H, s), 1.7–1.9(10H, m), 2.25 (1H, bs), 2.61(1H, bs), 3.69(3H, s), 4.33(1H, bs), 5.61(1H, s) | (FAB) 223 (MH+) |
| 5 | 1.4–2.2(15H, m), 2.41(1H, d, J=7.6Hz), 2.45(1H, d, J=7.6Hz), 3.67(1.5H, s), 3.67(1.5H, s) | (FAB) 223 (M–H)– |
| 6 | 1.4–2.2(15H, m), 2.45(1H, d, J=7.6Hz), 2.49(1H, d, J=7.6Hz) | (FAB) 209 (M–H)– |

TABLE 3-continued

| Ref. Ex. No | $^1$H-NMR(CDCl$_3$)δ(ppm) | MS |
|---|---|---|
| 7 | 1.9–2.1(10H, m), 2.35(1H, bs), 2.64 (2H, bs), 3.26(3H, s) | |
| 8 | 1.7–1.9(10H, m), 2.26(1H, bs), 2.63 (1H, bs), 3.23(3H, s), 3.69(3H, s), 4.24(1H, bs), 5.61(1H, s) | (FAB) 237 (MH+) |
| 9 | 1.3–2.2(14H, m), 2.41(1H, d, J=7.3Hz), 2.45(1H, d, J=7.6Hz), 3.23(1.5H, s), 3.23(1.5H, s), 3.67(1.5H, s), 3.67 (1.5H, s) | (FAB) 237 (M–H)– |
| 10 | 1.3–2.2(14H, m), 2.38(1H, d, J=7.9Hz), 2.41(1H, d, J=7.6Hz), 3.17(3H, s) | |

Data of the compounds of the referential examples 5, 6, 9 and 10 are shown as a mixture of stereoisomer (a mixture 1:1 measured by gas chromatography).

TABLE 4

| Exam. No | $^1$H-NMR(CDCl$_3$)δ(ppm) | MS (FAB) |
|---|---|---|
| 1 | 1.4–2.0(27H, m), 2.3–2.7(6H, m) | 288 (MH+) |
| 2 | 1.3–2.2(27H, m), 2.4–2.5(2H, m), 2.6–2.7(4H, m) | 304 (MH+) |
| 3 | 1.4–2.3(26H, m), 2.4–2.5(2H, m), 2.5–2.6(4H, m) | 322 (MH+) |
| 4 | 1.3–2.2(26H, m), 2.4–2.5(2H, m), 2.6–2.7(4H, m), 3.2(1.5H, s), 3.24 (1.5H, s) | 318 (MH+) |
| 5 | 1.2–1.9(27H, m), 2.3–2.4(2H, m), 2.5–2.6(4H, m) | 288 (MH+) |
| 6 | 0.78(3H, s), 1.2–2.0(26H, m), 2.3–2.4(2H, m), 2.5–2.6(4H, m) | 302 (MH+) |
| 7 | 1.5–2.2(30H, m), 2.3–2.4(2H, m), 3.01(2H, dd, J=7.3, 7.6Hz), 3.6–3.7 (1H, m) | 314 (MH+) |
| 8 | 1.3–2.1(30H, m), 2.3–2.4(2H, m), 3.01(2H, dd, J=7.3, 7.6Hz), 3.6–3.7 (1H, m) | 330 (MH+) |
| 9 | 1.4–2.1(29H, m), 2.2–2.3(2H, m), 3.00(2H, t, J=8.6Hz), 3.6–3.7(1H, m) | 348 (MH+) |
| 10 | 1.4–2.1(29H, m), 2.2–2.3(2H, m), 2.8–2.9(2H, m), 3.23(3H, s), 3.4– 3.5(1H, m) | 344 (MH+) |
| 11 | 1.4–2.0(30H, m), 2.1–2.2(2H, m), 2.7–2.8(2H, m), 3.2–3.3(1H, m) | 314 (MH+) |
| 12 | 0.78(3H, s), 1.2–2.0(29H, m), 2.2–2.3(2H, m), 2.9–3.0(2H, m), 3.5–3.6(1H, m) | 328 (MH+) |

Data of the compounds of the examples 2, 3, 4, 8, 9 and 10 are shown as a mixture of stereoisomer (a mixture 1:1 measured by gas chromatography).

We claim:

1. A compound of the formula (1)

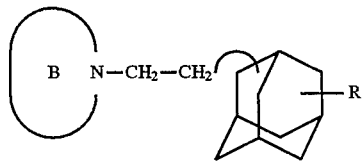

(1)

wherein heterocyclic group B is 3-azabicyclo[3.2.2] nonane-3-yl or 4-azatricyclo [4.3.1.1$^{3.8}$] undecane-4-yl, and R is hydrogen, lower alkyl, lower alkoxy, hydroxyl or halogen, or nontoxic salt thereof.

2. The compound according to claim 1 which is 2-(2-adamantyl) ethyl derivative (11) of the formula

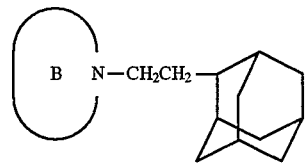

(11)

wherein heterocyclic group B is 3-azabicyclo[3.2.2] nonane-3-yl or 4-azatricyclo [4.3.1.1$^{3.8}$] undecane-4-yl or nontoxic salt thereof, 2-(1-adamantyl) ethyl derivative (12) of the formula

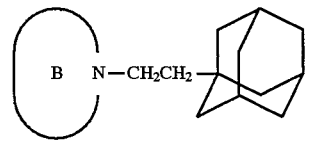

(12)

wherein heterocyclic group B has the same meaning hereinabove or nontoxic salt thereof, stereoisomer or mixture thereof of 2-(5-substituted-2-adadmantyl) ethyl derivative of the formula (13)

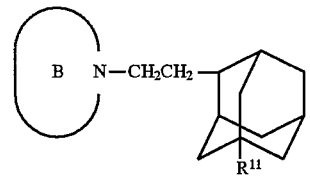

(13)

wherein R$^{11}$ is lower alkyl, lower alkoxy, hydroxy or halogen, and heterocyclic group B has the same meaning hereinabove or nontoxic salt thereof, or 2-(3-substituted-1-adadmantyl)ethyl derivative of the formula (14)

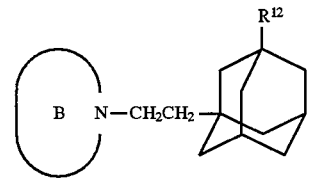

(14)

wherein R$^{12}$ is lower alkyl, lower alkoxy, hydroxy or halogen, and heterocyclic group B has the same meaning hereinabove or nontoxic salt thereof.

3. The compound according to claim 2 wherein 2-(2-adamantyl) ethyl derivative is
   3-[2-(2-adamantyl)ethyl]-3-azabicyclo[3.2.2] nonane or
   4-[2-(2-adamntyl)ethyl]-4-azatricyclo[4.3.1.1$^{3.8}$] undecane or nontoxic salt thereof.

4. The compound according to claim 2 wherein 2-(1-adamantyl) ethyl derivative is
   3-[2-(1-adamantyl)ethyl]-3-azabicyclo[3.2.2] nonane or
   4-[2-(1-adamantyl)ethyl]-4-azatricyclo[4.3.1.1$^{3.8}$] undecane or nontoxic salt thereof.

5. The compound according to claim 2 wherein 2-(5-substituted-2-adamantyl) ethyl derivative is a stereoisomer or mixture thereof of
   3-[2-(5-hydroxy-2-adamantyl)ethyl]-3-azabicyclo[3.2.2] nonane,
   3-[2-(5-chloro-2-adamantyl)ethyl]-3-azabicyclo[3.2.2] nonane, 3-[2-(5-methoxy-2-adamantyl)ethyl]-3-azabicyclo[3.2.2]
    nonane, 4-[2-(5-hydroxy-2-adamantyl)ethyl]-4-azatricyclo
    [4.3.1.1$^{3.8}$] undecane 4-[2-(5-chloro-2-adamantyl)ethyl]-4-azatricyclo
    [4.3.1.1$^{3.8}$] undecane or 4-[2-(5-methoxy-2-adamantyl)ethyl]-4-azatricyclo
    [4.3.1.1$^{3.8}$] undecane or nontoxic salt thereof.

6. The compound according to claim 2 wherein 2-(3-substituted-1-adamantyl) ethyl derivative is 3-[2-(3-methyl-1-adamantyl)ethyl]-3-azabicyclo[3.2.2]
    nonane or 4-[2-(3-methyl-1-adamantyl)ethyl]-4-azatricyclo
    [4.3.1.1$^{3.8}$] undecane or nontoxic salt thereof.

7. A process for production of a compound (1) of the formula

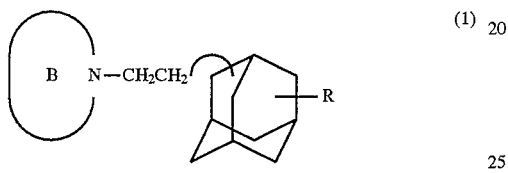 (1)

wherein heterocyclic group B is 3-azabicyclo[3.2.2] nonane-3-yl or 4-azatricyclo [4.3.1.1$^{3.8}$] undecane-4-yl, and R is hydrogen, lower alkyl, lower alkoxy, hydroxyl or halogen, or nontoxic salt thereof comprising reducing a carbonyl group (2) of the formula

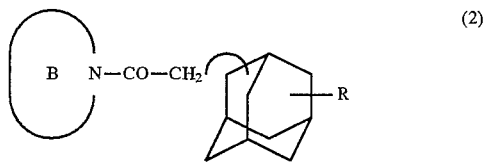 (2)

wherein heterocyclic group B and R have the same meanings hereinabove, and converting the compound to nontoxic salt thereof.

8. The process according to claim 7 in which the compound is 2-(2-adamantyl) ethyl derivative of the formula (11)

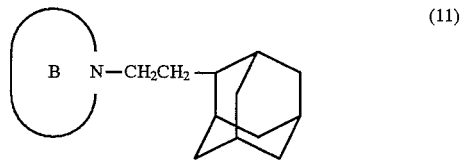 (11)

wherein heterocyclic group B is 3-azabicyclo[3.2.2] nonane-3-yl or 4-azatricyclo [4.3.1.1$^{3.8}$] undecane-4-yl, 2-(1-adamantyl) ethyl derivative of the formula (12)

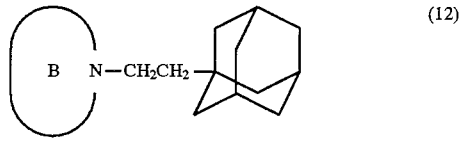 (12)

wherein heterocyclic group B has the same meanings hereinabove, stereoisomer or mixture thefor of 2-(5-substituted-2-adamantyl) ethyl derivative of the formula (13)

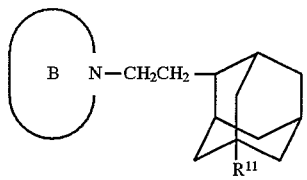 (13)

wherein R$^{11}$ is lower alkyl, lower alkoxy, hydroxy or halogen, and heterocyclic group B has the same meaning hereinabove, or 2-(3-substituted-1-adadmantyl)ethyl derivative of the formula (14)

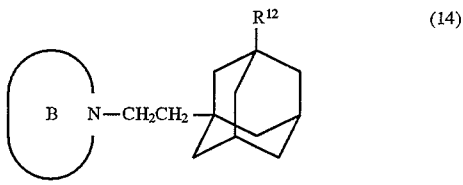 (14)

wherein R$^{12}$ is lower alkyl, lower alkoxy, hydroxy or halogen, and heterocyclic group B has the same meaning hereinabove.

9. The process according to claim 8 wherein 2-(2-adamantyl) ethyl derivative is

3-[2-(2-adamantyl)ethyl]-3-azabicyclo[3.2.2] nonane or

4-[2-(2-adamantyl)ethyl]-4-azatricyclo[4.3.1.1$^{3.8}$] undecane.

10. The process according to claim 8 wherein 2-(1-adamantyl) ethyl derivative is 3-[2-(1-adamantyl)ethyl]-3-azabicyclo[3.2.2] nonane or 4-[2-(1-adamantyl)ethyl]-4-azatricyclo[4.3.1.1$^{3.8}$] undecane.

11. The process according to claim 8 wherein 2-(5-substituted-2-adamantyl) ethyl derivative is a stereoisomer or mixture thereof of 3-[2-(5-hydroxy-2-adamantyl)ethyl]-3-azabicyclo[3.2.2]
    nonane, 3-[2-(5-chloro-2-adamantyl)ethyl]-3-azabicyclo[3.2.2]
    nonane, 3-[2-(5-methoxy-2-adamantyl)ethyl]-3-azabicyclo[3.2.2]
    nonane, 4-[2-(5-hydroxy-2-adamantyl)ethyl]-4-azatricyclo
    [4.3.1.1$^{3.8}$] undecane, 4-[2-(5-chloro-2-adamantyl)ethyl]-4-azatricyclo
    [4.3.1.1$^{3.8}$] undecane or 4-[2-(5-methoxy-2-adamantyl)ethyl]-4-azatricyclo
    [4.3.1.1$^{3.8}$] undecane.

12. The process according to claim 8 wherein 2-(3-substituted-1-adamantyl) ethyl derivative is 3-[2-(3-methyl-1-adamantyl)ethyl]-3-azabicyclo[3.2.2]
    nonane or 4-[2-(3-methyl-1-adamantyl)ethyl]-4-azatricyclo
    [4.3.1.1$^{3.8}$] undecane.

13. A medicament for treatment of schizophrenia containing the compound of the formula (1)

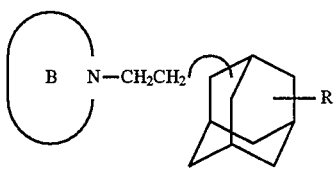

wherein heterocyclic group B is 3-azabicyclo[3.2.2] nonane-3-yl or 4-azatricyclo [4.3.1.1$^{3.8}$] undecane-4-yl, and R is hydrogen, lower alkyl, lower alkoxy, hydroxyl or halogen, or nontoxic salt thereof as an active ingredient.

14. A medicament for treatment of schizophrenia according to claim 13 in which the compound is 2-(2-adamantyl) ethyl derivative (11) of the formula

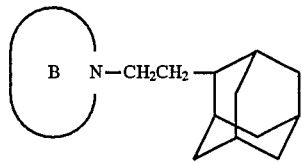

wherein heterocyclic group B is 8-azabicyclo[3.2.2] nonane-3-yl or 4-azatricyclo [4.3.1.1$^{3.8}$] undecane-4-yl, 2-(1-adamantyl)ethyl derivative (12) of the formula

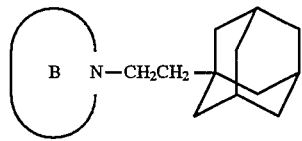

wherein heterocyclic group B has the same meaning hereinabove, stereoisomer or mixture thereof of 2-(5-substituted-2-adadmantyl) ethyl derivative of the formula (13)

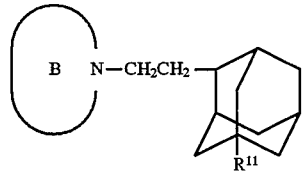

wherein R$^{11}$ is lower alkyl, lower alkoxy, hydroxy or halogen, and heterocyclic group B has the same meaning hereinabove, or 2-(3-substituted-1-adadmantyl)ethyl derivative of the formula (14)

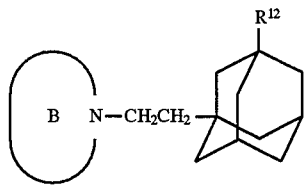

wherein R$^{12}$ is lower alkyl, lower alkoxy, hydroxy or halogen, and heterocyclic group B has the same meaning hereinabove.

15. The medicament for treatment of schizophrenia according to claim 14 wherein 2-(2-adamantyl)ethyl derivative is 3-[2-(2-adamantyt)ethyl]-3-azabicyclo[3.2.2] nonane or 4-[2-(2-adamantyl)ethyl]-4-azatricyclo[4.3.1.1$^{3.8}$] undecane.

16. The medicament for treatment of schizophrenia according to claim 14 wherein 2-(1-adamantyl) ethyl derivative is 3-[2-(1-adamantyl)ethyl]-3-azabicyclo[3.2.2] nonane or 4-[2-(1-adamantyl)ethyl]-4-azatricyclo[4.3.1.1$^{3.8}$] undecane.

17. The medicament for treatment of schizophrenia according to claim 14 wherein 2-(5-substituted-2-adamantyl)ethyl derivative is a stereoisomer or mixture thereof of 3-[2-(5-hydroxy-2-adamantyl)ethyl]-3-azabicyclo[3.2.2] nonane, 3-[2-(5-chloro-2-adamantyl)ethyl]-3-azabicyclo[3.2.2] nonane, 3-[2-(5-methoxy-2-adamantyl)ethyl]-3-azabicyclo[3.2.2] nonane, 4-[2-(5-hydroxy-2-adamantyl)ethyl]-4-azatricyclo [4.3.1.1$^{3.8}$] undecane, 4-[2-(5-chloro-2-adamantyl)ethyl]-4-azatricyclo [4.3.1.1$^{3.8}$] undecane or 4-[2-(5-methoxy-2-adamantyl)ethyl]-4-azatricyclo [4.3.1.1$^{3.8}$] undecane.

18. The medicament for treatment of schizophrenia according to claim 14 wherein 2-(3-substituted-1-adamantyl) ethyl derivative is 3-[2-(3-methyl-1-adamantyl)ethyl]-3-azabicyclo[3.2.2] nonane or 4-[2-(3-methyl-1-adamantyl)ethyl]-4-azatricyclo [4.3.1.1$^{3.8}$] undecane.

* * * * *